United States Patent [19]

Harris et al.

[11] Patent Number: 4,642,362
[45] Date of Patent: Feb. 10, 1987

[54] POLYMER BOUND CALIXARENES

[75] Inventors: Stephen J. Harris, Ballinteer; John G. Woods, Stillorgan; John M. Rooney, Naas, all of Ireland

[73] Assignee: Loctite (Ireland) Limited, Dublin, Ireland

[21] Appl. No.: 717,251

[22] Filed: Mar. 28, 1985

Related U.S. Application Data

[63] Continuation-in-part of Ser. No. 673,621, Nov. 21, 1984, Pat. No. 4,556,700, and a continuation-in-part of Ser. No. 575,257, Jan. 30, 1984, abandoned.

[51] Int. Cl.$^4$ ............................................. C07F 7/10
[52] U.S. Cl. .................................... 556/419; 556/437; 556/446; 556/449
[58] Field of Search ................. 556/419, 437, 446, 449

[56] References Cited

U.S. PATENT DOCUMENTS

| | | | | |
|---|---|---|---|---|
| 4,256,859 | 3/1981 | Woo | ..................... | 525/384 |
| 4,259,464 | 3/1981 | Buriks et al. | ..................... | 525/480 |
| 4,278,784 | 7/1981 | Wong | ..................... | 528/27 |
| 4,306,073 | 12/1981 | Darms et al. | ..................... | 556/419 |
| 4,447,585 | 5/1984 | Parker | ..................... | 525/359.2 |
| 4,556,700 | 12/1985 | Harris et al. | ..................... | 526/209 |
| 4,585,885 | 4/1986 | Bernhard et al. | ..................... | 556/436 |

OTHER PUBLICATIONS

Journal Inclusion Phenomenon, 2, 199–206, (1984).
Chem. Letters, 477–478, (1984).
J. Chem. Soc., Chem. Comm., 981–982, (1984).
Acc. Chem. Res., 16, 161–170, (1983).
Macromolecules Chem. Rapid Comm., 3, 705–707C, (1982).
JACS 103, 3782–3792, (1981).
Macromolecules 6, 133–142, (1973).
J. Polymer Scien., Polymer Chem. ed., 15, 1189–1197, (1977).
Topics in Current Chemistry (Structural Chemistry), 123, 1–47, (1984).

*Primary Examiner*—Lucille M. Phynes
*Attorney, Agent, or Firm*—Walter J. Steinkraus; Eugene F. Miller

[57] ABSTRACT

A linear or cross-linked polymer selected from polythioethers, polyethers, styrenic polymers, polyacrylates, and polyorganosiloxanes having a plurality of calixarene groups bound thereon, the calixarene groups having the formula

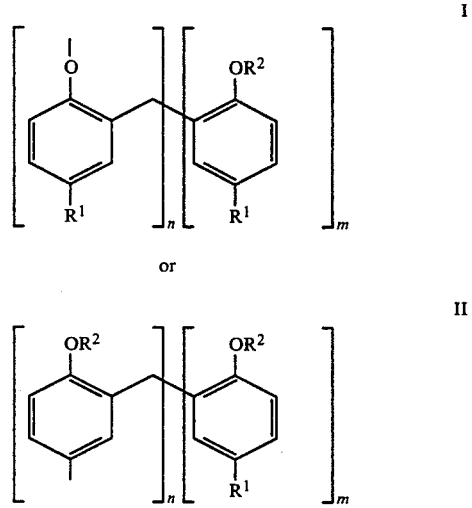

where the $R^1$ groups are the same or different H or hydrocarbyl groups; the $R^2$ groups are H, hydrocarbyl, —$CH_2C(=O)OR^3$, —$CH_2C(=O)R^3$, or —$C(=O)NHR^3$, $R^3$ is hydrocarbyl or substituted hydrocarbyl; n is an integer of 1–8, m is an integer of 0–7 and n+m is 4–8.

1 Claim, No Drawings

POLYMER BOUND CALIXARENES

This application is a continuation, in-part, of co-pending application Ser. No. 673,621 filed Nov. 21, 1984 now U.S. Pat. No. 4,556,700, as a continuation, in part, of Ser. No. 575,257, filed Jan. 30, 1984, abandoned.

BACKGROUND OF THE INVENTION

The ion complexation and enzyme mimic abilities of cyclic phenol—formaldehyde resins known as calixarenes have recently been reported in such references as Acc. Chem. Res., 16, 161–170 (1983); Makromol. Chem. Rapid Communications, 3 705–707 (1982); and JACS, 103 3782–3792 (1981). In co-pending applications Ser. Nos. 673,621 and 676,959, there are described novel calixarene compounds of the formula:

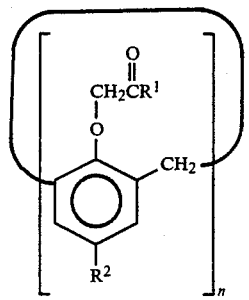

where $R^1$ is alkyl, alkoxy, substituted alkyl or substituted alkoxy; $R^2$ is H or alkyl; and n=4, 6, or 8. which are particularly useful as storage stable accelerators for cyanoacrylate "instant adhesive" monomer compositions. While a wide variety of calixarene structures and uses are known, heretofore the only suggestion to prepare polymer materials with calixarene moieties attached thereto has been the reaction of diepoxides, polycarboxylic acids or polyamines with calixarene hydroxyl groups, U.S. Pat. No. 4,259,464.

Polymer bound ethers and cryptate compounds, also known for ion complexing abilities, have been reported in such references as U.S. Pat. Nos. 4,256,859; 4,278,784; 4,447,585; J. Polymer Sci., Polymer Chem. ed., 15 1189–1197 (1977); and Macromolecules, 6 133–142 (1973).

SUMMARY OF THE INVENTION

The invention of this application is novel polymer structures selected from polythioethers, polyethers, styrenic polymers, polyacrylates and polyorganosiloxanes, which include at least one calixarene group bound thereto selected from:

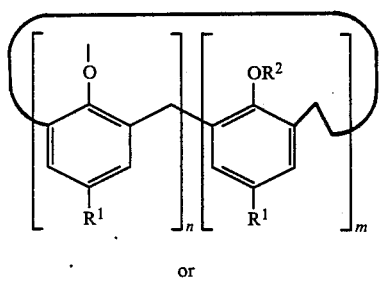

or

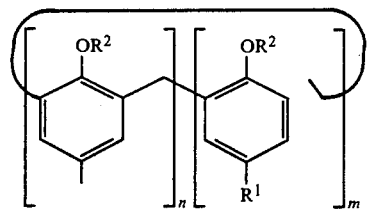

where the $R^1$ groups are the same or different H or hydrocarbyl groups; the $R^2$ groups are H, hydrocarbyl, $-CH_2C(=O)OR^3$, $-CH_2C(=O)R^3$, or $-C(=O)NHR^3$, $R^3$ is hydrocarbyl or substituted hydrocarbyl; n is an integer of 1–8, m is an integer of 0–7 and n+m is 4–8.

The calixarene groups may be terminally or pendently attached to the polymer backbone. The calixarene groups may also be part of a linear or a cross-linked polymeric backbone.

The polymers are useful as ion exchange resins, phase transfer catalysts, and as coatings, adhesives, or potting materials, especially in electronic applications.

A further aspect of the invention are novel dietherified calix(4)arenes from which a wide variety of linear calixarene containing polymers may be prepared.

A still further aspect of the invention are novel curable compositions employing functionalized calixarene cross-linking agents.

DETAILED DESCRIPTION OF THE INVENTION

Polymer bound calixarene moieties may be incorporated into a wide variety of polymers, including silicones, polyacrylates, polyethers, polyurethanes, polythioethers, and styrene polymers or co-polymers. For instance, calixarenes of the formula:

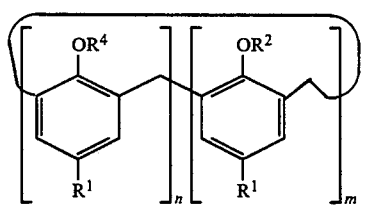

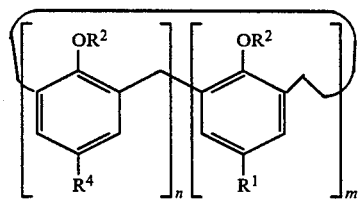

where $R^4$ is are alkenyl, alkynyl, or (meth)acryl can be polymer bound by hydrosilation or thiol-ene addition reactions using plural SiH or SH functional compounds. Additionally, such calixarenes, especially the (meth)acrylate functional calixarenes may be polymerized free radically using standard peroxide, azo, or photo initiators. Still another polymer binding approach is to react parent hydroxy calixarenes or calixarenes having alkyl hydroxy, alkyl thiol or amino functionality, with polyisocyanates in the conventional manner.

Still further, compounds or resins with plural alkyl halo functionality may be reacted (a) with calixarene phenolic hydroxyls or their alkaline metal salts to give polyethers, or (b) using Friedel-Crafts chemistry, with calixarenes unsubstituted in the para position to give polymer bound calixarenes linked through p-alkylene groups. Some of these reactions schemes are shown in the following equations:

RTV silicone using trialkoxysilylcalixarene cross-linker 4 (CH₃CH₂O)₃SiH +

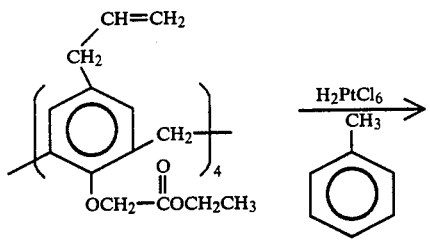

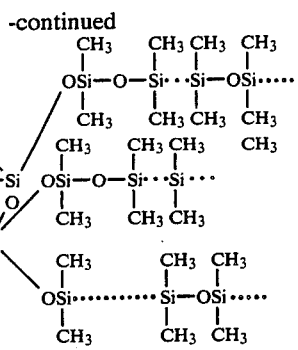

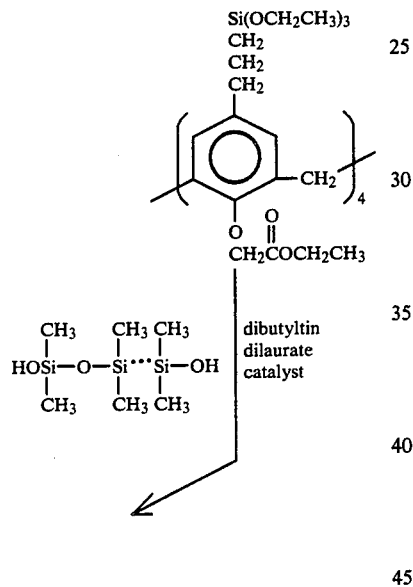

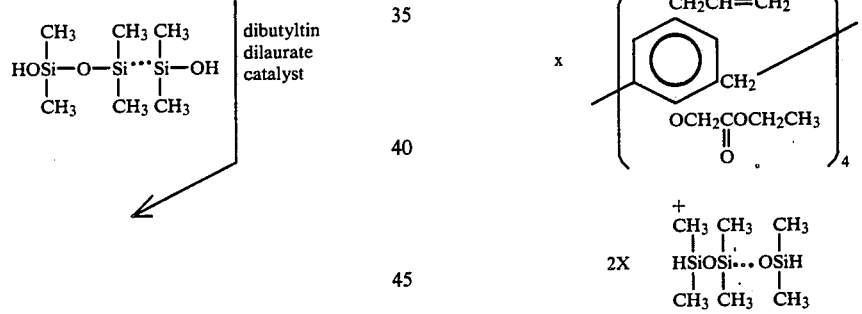

Alkenyl calixarenes cross-linked with SiH functional silicone

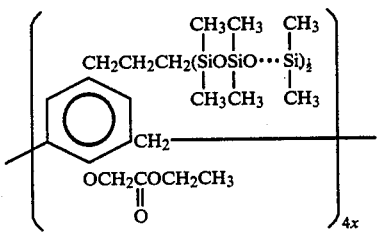

Alkenyl calixarenes cross-linked with polythiol to give polythioeters

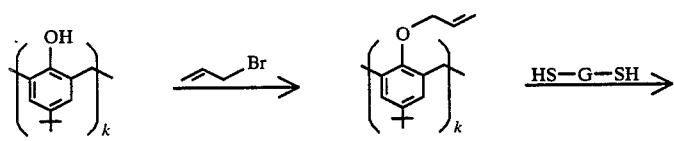

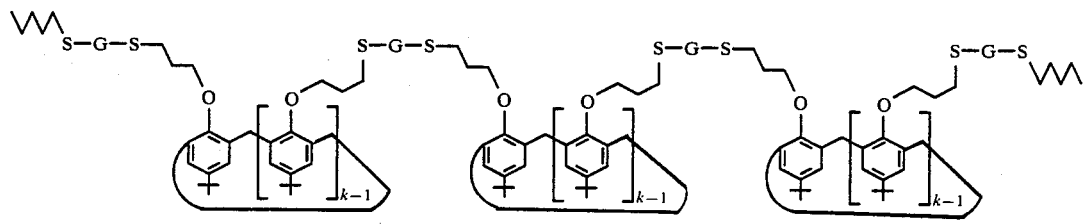

Calixarene (meth)acrylates

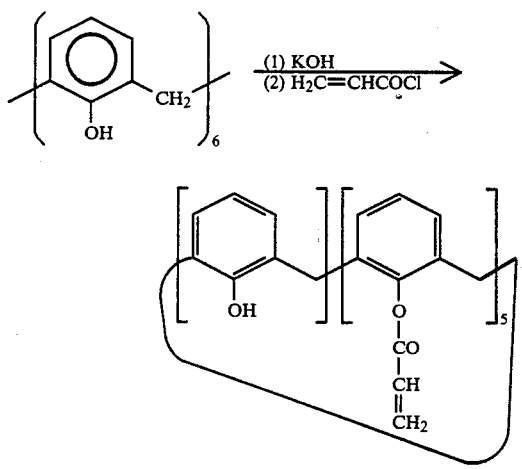

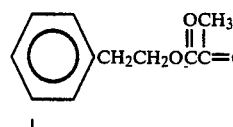

2,2-dimethoxy-
2-phenyl
acetophenone

UV co-polymer
insoluble in all common
organic solvents.

In addition to reaction with acid halides, (meth)acryl-calixarenes may be prepared by reaction of calixarene hydroxyl groups with isocyanato functional (meth)acrylate compounds, such as isocyanotoethyl methacrylate or acrylate, or by the two step reaction with diisocyanates and hydroxy functional (meth)acrylates.

Calixarene polyurethanes

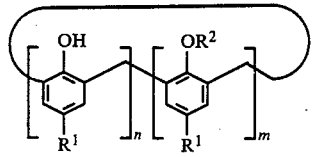

+

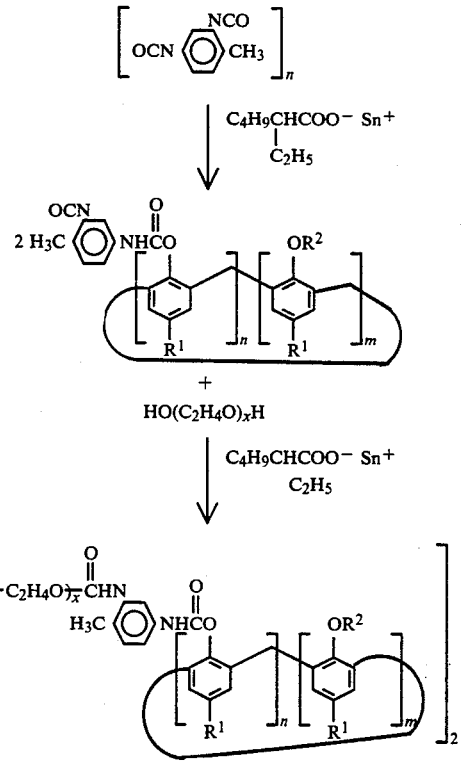

Calixarenes bound to polymers with reactive halogen
(a) etherification of phenolic hydroxyls Merrifield Polymer
(Swollen with $CH_2Cl_2$)

+

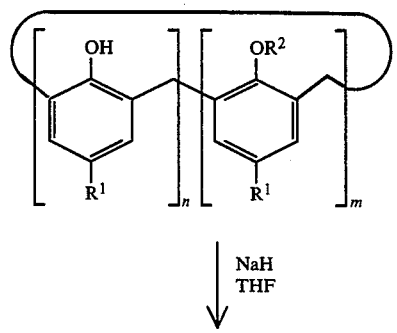

NaH
THF

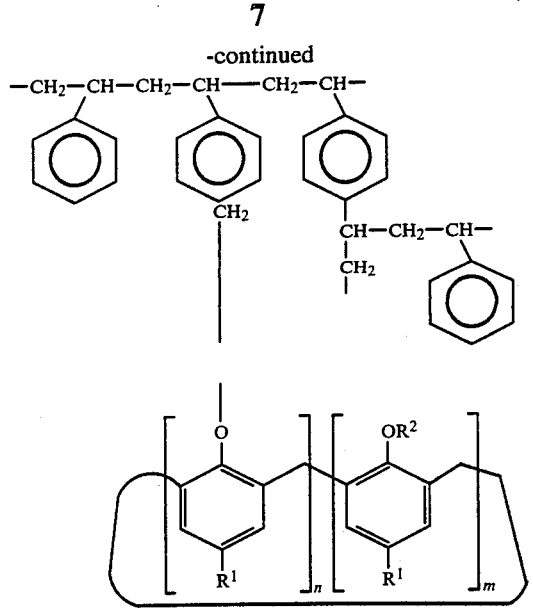

Calixarenes bound to polymers with reactive halogen
(b) Friedel-Crafts reaction

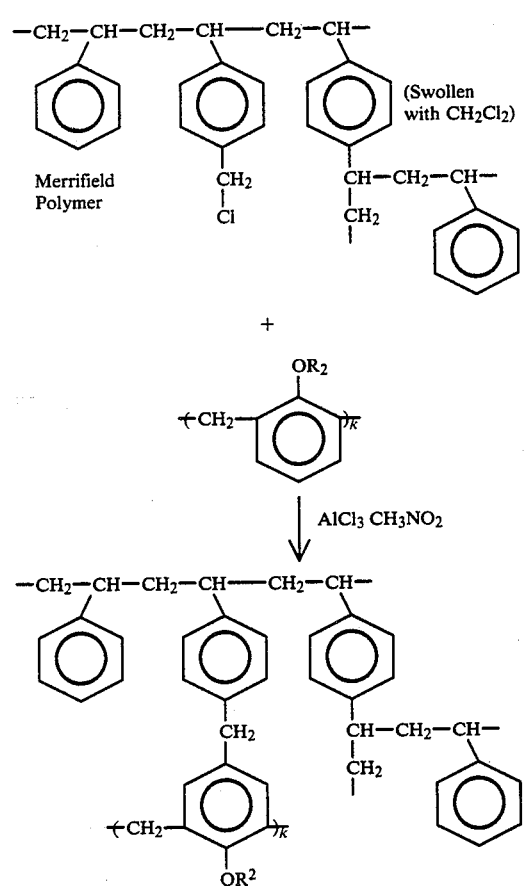

In the formulas I and II above, it is preferred that the R² groups are selected from hydrocarbyl and R⁵—COCH₂— groups, where R⁵ is selected from hydrocarbyl, —O—hydrocarbyl or —NH—hydrocarbyl groups. The R¹ groups of formulas I and II may be any hydrocarbyl group but are most preferably selected from H and alkyl, especially H or t-butyl.

The polymer bound calixarenes of the invention are metal ion sequestrants and are, therefore, useful as coatings and encapsulants for ion selective substrates such as electronic circuit boards; as solubilizing agents for ionic materials in polymeric media; and as recoverable phase transfer catalysts.

The invention may be illustrated by reference to the following non-limiting examples:

EXAMPLE 1

Preparation of Dietherified Calix(4)arene

A mixture of 1.62 g of 5,11,17,23-tetra-tert-butyl calix(4)arene, 2.0 g of ethyl bromoacetate, 2.07 g of anhydrous potassium carbonate, and 20 milliliters of dried DMSO was stirred for 48 hours under nitrogen at room temperature. At the end of this time, the mixture was poured into 200 milliliters of a 10% solution of aqueous hydrochloric acid. The precipitated off-white solid was filtered and washed twice with distilled water to yield 2.0 g of crude product. Recrystallization of this material from hot ethanol gave 1.64 g of a crystalline product (M.Pt.=173°-175° C.) which was characterized by i.r. and n.m.r. spectroscopy as the dietherified calix(4)arene:

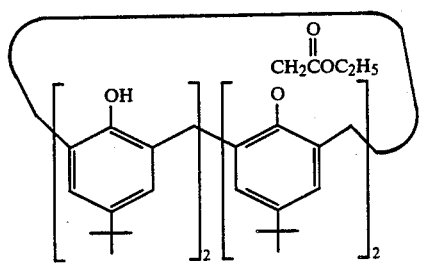

Elemental analysis: (Calc'd for $C_{52}H_{68}O_8$, C: 76.04, H: 8.36 O: 15.59; Found, C: 75.59, H: 8.31, O: 16.03).

EXAMPLE 2

A mixture of 1.65 g of dietherified calix(4)arene prepared as in Example 1, 0.096 g of sodium hydride, and 25 milliliters of dry THF was refluxed for twenty-one hours under nitrogen and then 0.585 g of allyl bromide was added dropwise over 10 minutes. The entire mixture was then refluxed for a further one hour, cooled and poured into 150 milliliters of a 10% solution of aqueous hydrochloric acid. The precipitated off-white solid was filtered and dried at 50° C. overnight. Recrystallization of this material from hot ethanol gave 1.5 g of a crystalline product (M.Pt.=167°-168° C.) which was characterized by i.r. and n.m.r. spectroscopy as a diallyl calix(4)arene:

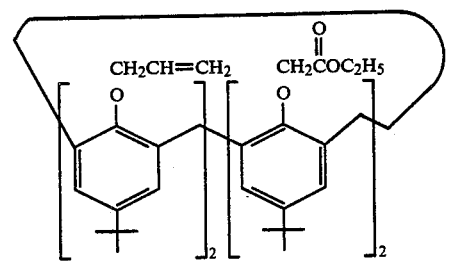

Elemental analysis: (Calc'd for $C_{58}H_{76}O_8$, C: 77.28, H: 8.52, O: 14.20; Found, C: 76.87, H: 8.35, O: 13.82).

EXAMPLE 3

Preparation of Calix(4)arene Diallylacetate Ester

A mixture of 1.9 g of dietherified calix(4)arene prepared as in Example 1. 1.04 g of allyl bromoacetate, and 1.0 g anhydrous potassium carbonate was heated to 130° C. under nitrogen with stirring for 30 minutes. The resulting solid mass was cooled and added to 100 milliliters of a 10% solution of aqueous hydrochloric acid. The undissolved solid was filtered, washed twice wit distilled water and dried overnight at 55° C. to give 2.7 g of crude product. Recrystallization of this material from hot ethanol yielded 2.1 g of a crystalline product (M.Pt.=115° C.) which was characterised by i.r. and n.m.r. spectroscopy as a diallyl ester of calix(4)arene.

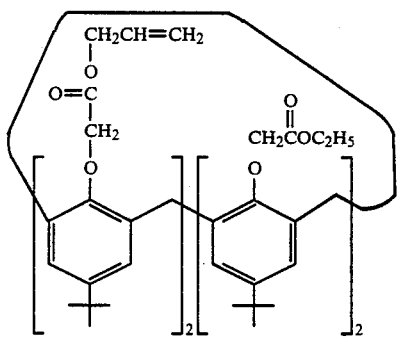

Elemental analysis: (Calc'd for $C_{62}H_{80}O_{12}$, C: 73.18, H: 7.94, O: 18.87; Found C: 73.24, H: 8.14, O: 19.08).

EXAMPLE 4

Preparation of Polyurethane-Bound Calixarene

A mixture of 0.339 g of dietherified calix(4)arene prepared as in Example 1, 0.144 g toluene diisocyanate, one drop of stannous octoate, and 5 milliliters of dried chlorobenzene was heated for 48 hours at 65° C. under nitrogen. To this mixture was added 0.83 g of poly(ethylene glycol) of molecular weight 2000 and the entire mixture was then heated for 24 hours at 65° C. After this time, infrared spectroscopic analysis indicated complete consumption of the isocyanate. The product was then precipitated with petroleum ether and characterized by i.r. spectroscopy and gel permeation chromatography as a polyurethane containing calixarene subunits.

EXAMPLE 5

Preparation of Silicone-Bound Calixarene

A mixture of 0.250 g of the diallyl calix(4)arene prepared as in Example 2, and 16 milliliters of dry toluene containing 50 parts per million of platinum (as dihydrogen hexachloroplatinate hexahydrate) was heated to 78° C. under nitrogen. To this mixture was added a solution of 0.277 g of a difunctional Si-H terminated polydimethylsiloxane resin of molecular weight 1010 in one milliliter of toluene gradually over 5 minutes. After a further 20 minutes at 78° C., volatiles were removed on a rotary evaporator yielding 0.484 g of a viscous, colorless oil, soluble in common organic solvents, which was characterized by infrared and n.m.r. spectroscopy and liquid chromatography as a low-molecular weight silicone polymer (mw ca 1950) containing calixarene subunits.

EXAMPLE 6

Preparation of Silicone-Bound Calixarene

A mixture of 0.305 g of the diallyl ester of calix(4)arene as prepared in Example 3, and 20 milliliters of dry toluene containing 50 parts per million of platinum (as dihydrogen hexachloroplatinate hexahydrate) was heated to 78° C. under nitrogen. To this mixture was added a solution of 0.303 g of a difunctional Si-H terminated polydimethylsiloxane resin of molecular weight 1010 in one milliliter of toluene gradually over 5 minutes. After a further 20 minutes at 78° C., volatiles were removed on a rotary evaporator yielding 0.63 g of a viscous, pale grey oil, solidifying on standing to a waxy solid which was soluble in common solvents and which was characterized by infrared and n.m.r. spectroscopy and liquid chromatography as a low-molecular weight silicone polymer (mw ca 2000) containing calixarene subunits.

EXAMPLE 7

Preparation of Calixarene-Containing Polyurethane Gel

To 0.212 g of unsubstituted calix(6)arene:

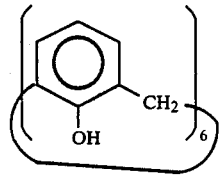

in 5 milliliters of dry dichloromethane was added 0.348 g of toluene diisocyanate and one drop of stannous octoate catalyst. This mixture was stirred for 24 hours under nitrogen at room temperature. After that time, infrared spectrophotometric analysis showed diminution of the band at 2260 cm$^{-1}$ attributable to the isocyanate group and the appearance of a new band at 1720 cm$^{-1}$ attributable to a carbamate carbonyl group. To the mixture was then added 2.0 g of poly(ethylene glycol) of molecular weight 2000 and the resulting mixture was stirred under nitrogen for 17 hours at room temperature to give a very viscous solution. Infrared analysis of this product showed no absorbance at 2260 cm$^{-1}$ indicating complete consumption of the isocyanate. The viscous solution gelled on further standing.

By use of chlorobenzene in place of dischloromethane and gradual removal of solvent in a mold it was possible to cast clear, colorless, brittle films of the material. The dried film was insoluble in common organic solvents, indicating substantial cross-linking.

EXAMPLE 8

Preparation of 5,11,17,23-Tetra-Allyl Calix(4)arene Ester

A mixture of 1.28 grams of unsubstituted calix(4)arene, 0.58 grams sodium hydride, and 25 milliliters of dry THF was refluxed for one hour under nitrogen. After this time, 2.92 grams of allyl bromide was added dropwise over 10 minutes. The entire mixture was then refluxed overnight. After cooling, the reaction mixture was treated with three milliliters of water, dried on a rotary evaporator under vacuum, dissolved in ether and extracted with an equal volume of water. The ether layer was then dried over magnesium sulfate and solvent was removed under vacuum to yield 1.38 grams of an off-white powder characterized by infrared spectroscopy as 25,26,27,28-tetra-allyloxy calix(4)arene.

This material was dissolved in 17 milliliters of dimethyl-p-toluidine and heated with stirring to 220° C. for 4 hours under nitrogen. The cooled solution was treated with dilute aqueous sulfuric acid precipitating a white solid which was washed with water and dried to yield 1.4 grams of a material characterized by infrared spectroscopy as 5,11,17,23-tetra-allyl calix(4)arene.

To this material (0.858 grams) was added 1.96 grams of ethyl bromoacetate, 1.22 grams potassium carbonate, and 20 milliliters of acetone. The entire mixture was refluxed under nitrogen for 5 days, poured into dilute aqueous sulfuric acid, extracted into dichloromethane, dried over magnesium sulfate and solvents were removed to yield 1.32 grams of a pale yellow oil characterized by infrared spectroscopy and liquid chromatography as 5,11,17,23-tetra-allyl 25,26,27,28-tetra-(2-ethoxy-2-oxo-)ethoxy calix(4)arene.

EXAMPLE 9

Preparation of Silicone-Bound Calixarene

A mixture of 0.149 grams of the tetra-allyl calixarene ester prepared in Example 8, and 10 milliliters of dry toluene containing 50 parts per million of platinum (as dihydrogen hexachloroplatinate hexahydrate) was heated to 80° C. under nitrogen. To this mixture was added a solution of 0.324 grams of a difunctional Si-H terminated polydimethylsiloxane resin of molecular weight 1010 in one milliliter of toluene over 5 minutes. After a further 20 minutes at 80° C., volatiles were removed on a rotary evaporator yielding 0.472 grams of a viscous pale yellow oil which was characterized by infrared spectroscopy and viscometry as a high polymer containing silicone and calixarene subunits.

EXAMPLE 10

Preparation of Calixarene-Containing Polystyrene Gel

A swollen cross-linked chloromethylated polystyrene matrix was prepared by treating 0.320 grams of a Merrifield polymer (200–400 mesh, 2% divinylbenzene, 5 mmol Cl/g) with dichloromethane for 15 minutes, filtering, and drying. The swollen polymer was then stirred together with 10 milliliters of dry nitromethane, 0.307 grams of 37,38,39,40,41,42-hexa(2-ethoxy-2-oxo)ethoxy calix(6)arene, and 0.214 grams of powdered anhydrous aluminum chloride at 100° C. for 10 minutes under nitrogen. The mixture was then maintained at 40° C. for 17 hours, poured into methanol, washed with a hot methanol/aqueous hydrochloric acid solution, with water, with methanol, and finally extracted with acetone for 5 hours to yield 0.221 grams of material characterized by infrared spectroscopy as a polystyrene gel containing bound calixarene units.

EXAMPLE 11

Preparation of Calixarene-Containing Polystyrene Gel

A swollen cross-linked chloromethylated polystyrene matrix was prepared as described in Example 10, and added to a mixture of 5 milliliters of dry THF, and 0.300 grams of the dietherified calix(4) arene described in Example 1 which had been pre-reacted with 0.019 grams of sodium hydride. This mixture was heated to reflux under nitrogen for 4 hours, then poured into methanol. The resulting yellow solid was washed and extracted as described in Example 10 to yield 0.263 grams of a pale yellow material which was characterized by infrared spectroscopy as a polystyrene gel containing bound calixarene units.

EXAMPLE 12

Ion Extraction by Polymer-Bound Calixarenes

The ion binding abilities of polymer-bound calixarenes were measured by extraction of metal picrates from aqueous into organic media. In each experiment a solution of the calixarene-containing polymer in dichloromethane was prepared such that the concentration of calixarene subunits was $2.5 \times 10^{-4}$M. A solution of picric acid in 0.1M aqueous sodium hydroxide was prepared such that the concention of sodium picrate was $2.5 \times 10^{-4}$M. Equal volumes of each solution (5 milliliters) were shaken together for 3 minutes and the percentage extraction of sodium picrate into the organic phase was determined by measuring the increase in absorbance of the dichloromethane layer at 387 nm in a spectrophotometer. The results are presented in Table 1.

TABLE 1

| Calixarene | Percentage Extraction |
| --- | --- |
| None | 0 |
| None; 18-Crown-6 | 13.5 |
| Example 1 | 1.4 |
| Example 2 | 56.9 |
| Example 3 | 85.0 |
| Example 4 | 9.0 |
| Example 5 | 6.0 |
| Example 6 | 32.0 |
| Example 9 | 34.5 |

EXAMPLE 13

Calixarene Polythioether

A formulation was prepared consisting of 1.0004 g of 5,11,17,23,29,35-hexa-t-butyl-37,38,39,40,41,42-hexa allyloxy calix(6)arene, 0.6032 g of pentaerythritol tetrakis(β-mercapto-propionate), 0.0351 g of 2,2-dimethoxy-2-phenyl acetophenone, 8.94 g of toluene, and 9.56 g of chloroform. This solution was coated onto a silicone-treated polyester film and irradiated under a medium-pressure Mercury arc at an intensity of 55 mw/cm$^2$ at 365 nm for 15 seconds followed by a post-bake at 90° C. for one hour to remove residual solvents. The formulation had cured to a brittle film.

EXAMPLE 14

Preparation and Copolymerization of Acrylated Calix(6)arene

To a mixture of 0.212 g of unsubstituted calix(6)arene in 10 milliliters of 2-methoxyethyl ether at 0° C. was added 0.336 g of potassium hydroxide dissolved in one milliliter of water. The resultant mixture was stirred while 0.546 of acryloyl chloride was added dropwise over 10 minutes. The reaction mixture was then warmed to room temperature while being stirred for a further 45 minutes. Filtration, washing three times with distilled water, and drying yielded 0.33 g of an off-white powder. Chromatography on an acid-washed alumina column using dichloromethane as eluent gave a colourless powdered product which was characterized by infrared and n.m.r. spectroscopy as the pentaacrylate of calix(6)arene. A solution was prepared consisting of 0.050 g of this acrylated calixarene, 1.0 g of tetrahydrofurfuryl acrylate, and 0.01 g of 2,2-dimethoxy-2-phenyl acetophenone. The solution was irradiated for 90 seconds under a medium-pressure mercury arc to yield a solid copolymer.

EXAMPLE 15

A formulation was prepared consisting of 0.1 gram of the acrylated calix(6)arene synthesized in Example 14, 1.0 gram of 2-phenylethyl methacrylate and 0.01 gram of 2,2-dimethoxy-2-phenyl acetophenone. A 2 mm thick film of this formulation in a mold was irradiated under a medium-pressure mercury arc for 180 seconds. At the end of this time, the formulation had hardened to a material insoluble in common organic solvents. A similar formlation but without the acrylated calix(6)arene, when irradiated under identical conditions, yielded only readily soluble material.

EXAMPLE 16

Alkoxysilane Calixarene Cross-Linked RTV Silicone

A mixture of 0.252 g of the product of Example 8 (0.00027 mole) and 10 mls dry toluene containing 50 ppm of platinum (as dihydrogen hexachloroplatinate hexahydrate) was heated to 80° C. under nitrogen. To this was added a solution of 0.178 g (0.00108 mole) triethoxysilane in 1 ml dry toluene (containing an identical level of platinum) during 10 minutes. After 30 minutes at 80° C. there was no indication of any reaction having taken place i.e. no reduction in peak in infra red spectrum at 1630 cm$^{-1}$ of C=C. The mixture was then taken to 120° C. (and left there for 96 hr.) and after this time reaction was adjudged to be complete, no peak at 1630 cm$^{-1}$, and volatiles were removed under reduced pressure to give 0.465 g ca 100% of a triethoxy silyl calix(4)arene of the formula:

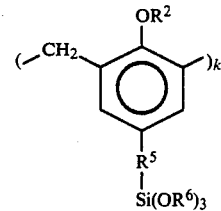

which was mixed with 4.65 g of polydimethylsiloxanediol of 50,000 cps viscosity and 0.046 g of stannous octanoate catalyst. The triethoxysilyl calixarene acted as a cross-linker, and in several hours a solid cured slug of clear colourless RTV silicone was produced. The vulcanized RTV silicone was insoluble in common solvents.

We claim:

1. A calixarene compound of the formula:

where $R^2$ is H, hydrocarbyl, $CH_2C(=O)OR^3$, $CH_2C(=O)R^3$ or $C(=O)NHR^3$; $R^3$ is hydrocarbyl; $R^5$ is alkylene or alkenylene; $R^6$ is alkyl or aryl; and k is 4–8.

* * * * *